(12) United States Patent
Percival et al.

(10) Patent No.: US 6,663,859 B2
(45) Date of Patent: Dec. 16, 2003

(54) COMPOSITIONS FOR ENHANCING THE IMMUNE RESPONSE

(75) Inventors: Susan S. Percival, Gainsville, FL (US); Robin J. Henken, Gainsville, FL (US); John St. Cyr, Coon Rapids, MN (US); Clarence A. Johnson, Wyoming, MN (US); Terri L. Butler, Minneapolis, MN (US)

(73) Assignees: Bioenergy, Inc., Ham Lake, MN (US); University of Florida, Gainesville, FL (US)

( * ) Notice: Subject to any disclaimer, the term of this patent is extended or adjusted under 35 U.S.C. 154(b) by 0 days.

(21) Appl. No.: 09/756,558

(22) Filed: Jan. 8, 2001

(65) Prior Publication Data

US 2002/0028196 A1 Mar. 7, 2002

Related U.S. Application Data

(60) Provisional application No. 60/175,050, filed on Jan. 7, 2000.

(51) Int. Cl.[7] ............... A01N 63/00; A61K 45/00; A61K 31/70; C12N 5/00
(52) U.S. Cl. ............ 424/93.71; 424/85.1; 424/85.2; 424/85.4; 424/85.5; 424/85.6; 424/85.7; 424/93.21; 424/93.2; 424/278.1; 424/400; 424/455; 424/489; 435/375; 514/43; 514/44; 514/45; 514/46; 514/47; 514/48; 514/49; 514/50; 514/51; 514/547; 514/549; 514/552; 514/558; 514/560; 514/885
(58) Field of Search ............ 424/93.71, 93.2, 424/93.21, 85.1, 400, 453, 489, 278.1, 85.2, 85.4, 85.5, 85.6, 85.7; 435/375; 514/43, 44, 45, 46, 47, 48, 49, 50, 51, 547, 549, 552, 558, 560, 885

(56) References Cited

U.S. PATENT DOCUMENTS

| | | | |
|---|---|---|---|
| 4,465,669 A | * | 8/1984 | Wissler et al. ............ 424/177 |
| 4,871,718 A | | 10/1989 | Carniglia ................... 514/23 |
| 4,923,851 A | * | 5/1990 | Carniglia |
| 5,177,065 A | | 1/1993 | Silvetti, Sr. et al. ......... 514/53 |
| 5,231,085 A | * | 7/1993 | Alexander et al. .......... 514/44 |
| 5,391,550 A | | 2/1995 | Carniglia et al. ............ 514/23 |
| 6,159,942 A | | 12/2000 | St. Cyr et al. .............. 514/23 |
| 6,159,943 A | | 12/2000 | Butler et al. ............... 514/23 |

OTHER PUBLICATIONS

Carver, J., et al.,"Dietary Nucleotide Effects upon Murine Natural Killer Cell Activity and Macrophage Activation", *Journal of Parenteral and Enteral Nutrition*, 14(1), (1990), pp. 18–22.

Kerr, D.J. ,et al. ,"Modulation of the immune response by thioureylene antithyroid drugs", *Abstract, Database CAPLUS on STN, No. 106:188814*, (1987), 1 page.

Matsumoto, Y., et al. ,"Nucleoside–Nucleotide Mixture Increases Peripheral Neutrophils in Cyclophosphamide–Induced Neutropenic Mice", *Nutrition*, 11(3), (1995), pp. 296–299.

Pisarev, V.M. ,et al. ,"Immunostimulating activity of 5'–phosphonates of nucleosides", *Abstract Database CAPLUS on STN No. 119:131115, Columbus, OH*, (1993), 1 page.

Zunica, G., et al., "D–Ribose Inhibits DNA Repair Synthesis in Human Lymphocytes", *Biochemical and Biophysical Research Communications*, 138(2), (1986), pp. 673–678.

* cited by examiner

*Primary Examiner*—Jon P. Weber
*Assistant Examiner*—Kailash C. Srivastava
(74) *Attorney, Agent, or Firm*—Kathleen R. Terry

(57) ABSTRACT

D-Ribose and methods for using D-Ribose are provided for enhancing the immune response in mammals. Those with a less than optimal immune response will benefit from oral or parenteral administration of D-Ribose. Methods are also provided for the enhancement of the immune response in isolated leukocytes. Leukocytes are cultured ex vivo in the presence of D-Ribose and transfused into a patient in need of leukocyte augmentation.

3 Claims, 4 Drawing Sheets

COMPOSITIONS FOR ENHANCING THE IMMUNE RESPONSE

This appln claims benefit of 60/175,050 Jan. 7, 2000.

FIELD OF THE INVENTION

The present invention relates to compositions and methods for enhancing the immune response in mammals. Such mammals include human infants, humans with depressed immune response and normal humans who would benefit from an enhanced immune response. The compositions may be applied in vivo or ex vivo.

BACKGROUND OF THE INVENTION

The immune system of mammals protects the host from microbial and viral invasion and is essential for survival. Individuals born with severe deficits in immunity must be confined to a sterile environment in order to survive. Individuals with acquired immunodeficiency due to infection with the human immunodeficiency virus or chemotherapy, can succumb to opportunistic infections that would not make a healthy human seriously ill. Even healthy humans experience episodes of infection from influenza, respiratory diseases, or such, which are caused by or result in a less than optimal immune function. Human infants, in particular, have immature immune systems and would benefit from compositions and methods effective to enhance their immune systems. The cells comprising the immune system may benefit from ex vivo enhancement of the immune response.

The immune system is complex. Following presentation of an antigen, as from a pathogenic microorganism or virus, cells of the lymphoid and myelogenous tissues undergo rapid clonal expansion. Including in these reacting cells are antigen-presenting macrophages which facilitate the introduction of antigen to B- and T-cells. T-cells include natural killer cells and T-helper cells, which enhance the ability of B-cells to make antigen-specific antibodies. All of these cells interact to suppress and eliminate the infection.

Lymphoid and myelogenous tissues at rest have a high rate of cell proliferation with a rapid protein turnover. When activated, these tissues have an even higher metabolic rate, the "respiratory burst." Oxygen and nutrient consumption increase many-fold as the cells proliferate, differentiate and produce antibodies and degradative proteins with which to combat the invading pathogen. It is well known that individuals with nutritional deficiencies are unable to mount an effective immune response. Among the deficiencies identified as contributing to a poor immune response are the lack of vitamins A, $B_1$, $B_2$, $B_6$, $B_{12}$, C, E and folic acid. Low protein and insufficient caloric intake also depress the immune response. Newborn infants have suboptimal immune responses and are susceptible to infection. When growth retardation, nutritional deficiency and low birth weight complicate the picture, impairment of immunocompetence is more marked. Elderly persons often have reduced immunocompetence due to the common occurrence of increased nutritional deficiencies at a time of life when better nutritional intake is necessary to compensate for decreased metabolic efficiency.

Among the conditions that are characterized by an impaired immune response are malignancies, chronic fatigue syndrome, cardiac cachexia, acute and chronic stress such as extreme physical activity or anxiety, depression, fungal infections, acute, subacute and chronic infection, diabetes, "jet lag" syndrome, eating disorders, and trauma including surgery, and the like. It is unknown whether the impairment of the immune system is the primary or contributory cause of these conditions, but it is well known that individuals suffering from these conditions are unable to mount a vigorous immune response and are especially susceptible to debilitating or even life-threatening infections ranging from the common cold to septic shock. Not wishing to be bound by theory, it is proposed that a method of enhancing the immune response, while not curing these conditions, would ameliorate some of the symptoms.

Because the proliferating and protein-synthesizing leukocytes have increased requirements for DNA and RNA, several researchers have administered nucleotides and/or nucleosides to provide pre-formed DNA and RNA. Typical of these studies is that of Carver et al. (Journal of Parenteral and Enteral Nutrition (1990) 14:18) where weanling mice fed up to 0.035% w/w nucleotides (Sigma Chemical, St. Louis, Mo.) show increased NK activity, macrophage activation and spleen weight. Other workers found that mice subjected to the chemotherapeutic agent cyclophosphamide or low protein diets, either of which depresses the immune system profoundly, were benefited from administration of a mixed nucleotide/nucleoside composition. (Adje et al. (1995) American Journal of Nutrition; Matsumoto et al. (1995) Nutrition 11:296.)

Several workers have found that adding the monosaccharide D-Ribose has a salutary effect on the enhancement of energy or the prevention of exercise-induced pain and cramping. See, for example, U.S. Pat. Nos. 6,159,942 and 6,159,943. The tissues involved in these studies were skeletal muscles. Nothing was known of the effect of D-Ribose on the immune response. It has been thought by those skilled in the art that D-Ribose was cytotoxic to a number of cells, including immune cells. Marini et al (Proceedings of the Society for Experimental Biology and Medicine (1985) 180:246–257) tested the effects of D-Ribose and deoxy-D-Ribose at levels from 12.5 to 50 mM on the incorporation of tritiated thymidine in various cell cultures and concluded: "they deeply derange metabolic processes in both dividing and nondividing cells."

A need remains for compositions and methods to enhance the immune response.

SUMMARY OF THE INVENTION

The present invention provides the administration of an effective dose of D-ribose to enhance the immune response in a mammal by inducing proliferation, differentiation and maturation of leukocytes. The D-Ribose may be administered orally or parenterally. A preferred effective dose is 0.2 to 20 gm of D-Ribose. A more preferred effective dose is 0.5 to 10 gm of D-Ribose. A most preferred effective dose is 0.5 to 5 gm of D-Ribose. The doses may be administered once, twice or three times per day. The leukocytes to be enhanced in vivo may be endogenous or obtained via an autogenous transfusion or a transfusion from a donor or donors. The D-Ribose may also be administered ex vivo to isolated immune cells, which are cultured in the presence of D-Ribose until proliferation and differentiation are achieved and then transfused into a recipient. The preferred concentration of D-Ribose in the culture medium is 2 to 20 mM, more preferably 5 to 15 mM and most preferably 10 mM.

DETAILED DESCRIPTION OF THE FIGURES

DETAILED DESCRIPTION OF THE INVENTION

Figure 1:
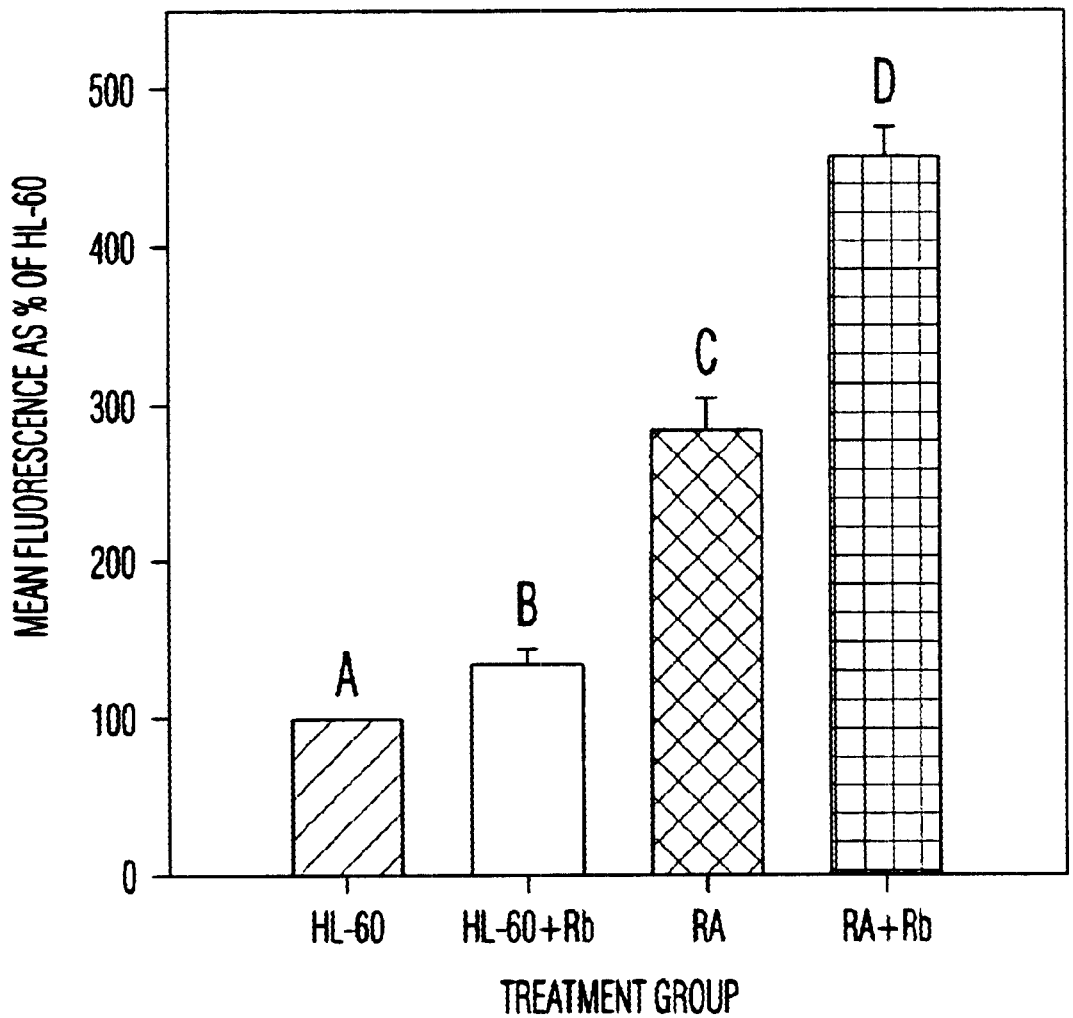
FIG. 1 shows the expression of mature cell markers on treated HL-60 cells.

D-Ribose is the sugar backbone and the initial substrate for the synthesis of RNA and DNA, both of which increase during the proliferation and differentiation of lymphoid tissue during the immune response. Because ribose can bypass the rate-limiting step in purine and pyrimidine synthesis, added ribose elevates the 5-phosphoribosyl-1-pyrophosphate (PRPP) pool, leading to greater DNA and RNA synthesis. Additionally, as more fully described in co-pending U.S. patent application Ser. No. 09/406,266, now U.S. Pat. No. 6,218,366, PRPP may protect from the free radicals formed during transient or localized hypoxia that may accompany the respiratory burst. Additionally, in co-pending U.S. patent application Ser. No. 09/290,789, now U.S. Pat. No. 6,159,942, it is shown that the administration of D-Ribose to healthy humans enhances the energy level of healthy males, as is seen in increased levels of skeletal muscle ATP and in increased power output.

It is a common medical procedure to draw blood from a donor, separate out the various components by centrifugation and transfuse the "buffy" layer of leukocytes into a recipient needing immune augmentation. Generally, the leukocytes from several donors are pooled for processing. The compositions and methods of this invention are beneficially applied ex vivo to the leukocytes to enhance differentiation before transfusion into the recipient.

Although it is not known which of these effects, or some unknown mechanism, leads to an increased immune response, it is here shown that D-Ribose, modifies immune cell function in lymphoid and myelogenous tissues both in vivo and ex vivo.

The invention is not limited to the following embodiments which are here disclosed for the purpose of demonstrating how the invention disclosed herein was made and to explain what is meant by enhancement of the immune response. It will be apparent to those skilled in the art that many modifications, variations or substitutions of the present invention can be readily made without undue experimentation. Therefore, such modifications, variations or substitutions are considered to be within the scope of the claims appended hereto.

EXAMPLE 1

In Vitro Studies with Human Cells

Cells in culture can be stimulated to proliferate by culturing in the presence of such mitogens as interleukine-2, PHA, specific antibodies to cell surface antigens, among others. For this study, cells that proliferate without mitogen stimulation were selected and retinoic acid was used for its known stimulation of differentiation.

A. Cell Culture

For the in vitro studies, HL-60 cells (American Type Culture Collection, Manassas, Va.), an immortal human lymphocyte cell line, at approximately passage twenty were maintained between $2.0 \times 10^5$ cells/ml in RPMI 1640 medium containing HEPES buffer (Cellgro, Mediatech Inc., Herdon, Va.), 2 mmol/L L-glutamine (Cellgro), 1% antimycotic (Cellgro), 10% heat treated fetal bovine serum (FBS: GibcoBRL; Life Technologies, Baltimore, Md.), and 0.1% gentamicin (GibcoBRL). Cultures were incubated at 37° C. with 5% $CO_2$ and humidity for the times indicated in the figures.

Experimental flasks were initiated at a concentration of $2.5 \times 10^5$ cells/ml. Differentiation of HL-60 cells was induced using all-trans retinoic acid (RA) prepared in 95% ethanol. RA was added to flasks at a concentration of 1.0 $\mu$mol/L such that the ethanol concentration added to the flask was less than 0.1%. D-Ribose preparations were made by dissolving powdered ribose (Bioenergy, Minneapolis, Minn.) in RPMI medium followed by sterile filtration.

The specificity of ribose, time and dose response was examined. The doses of ribose were 1, 5, 10, 25 and 50 mmol/L. In experiments in which one concentration of ribose was used, 10 mmol/L was the dose chosen. The effect of timing of the dose was explored by adding ribose at various times after the addition of the retinoic acid. Specificity was examined by substituting glucose, to eliminate the nonspecific effects of ribose as a substrate for glycolysis or gluconeogenesis, or change in osmolarity.

Following ninety-six hours of incubated (or as specified), cells were harvested, counted by hemocytometer and viability assessed using trypan dye exclusion. For growth and viability determinations, cells were counted three times within one experiment. Results shown were from at least three experiments. Cells were washed twice with phosphate buffered salt solution (PBS) and brought to a concentration of $2.0 \times 10^7$ cells/ml PBS. Table 1 shows the results.

TABLE 1

Cellular Proliferation and Viability of HL-60 Cells with D-Ribose and/or Retinoic Acid

| Treatment | Cell Growth ($10^5$ cells/ml) | Viability (%) |
|---|---|---|
| HL-60 (control) | 10.24 +/− 1.94 | 92.3 +/− 2.1 |
| HL-60 + D-Ribose | 6.68 +/− 1.29 | 86.3 +/− 5.5 |
| HL-60 + RA | 7.01 +/− 2.14 | 84.5 +/− 4.8 |
| HL-60 + RA + D-Ribose | 3.08 +/− 0.83 | 63.9 +/− 9.6 |

As can be seen from Table 1, cellular growth was reduced when cells were treated with either RA or ribose. The initial cell density was $2.5 \times 10^5$. The HL-60 cells quadrupled in number over the 96-hour incubation period; the RA or D-Ribose treated cells nearly tripled in number; while the cells treated with both RA and D-Ribose barely increased in number. When compared to control HL-60 cells, cells incubated with RA and ribose showed a 70% reduction in cell growth while cells incubated with RA or ribose alone showed a 30% decline. A similar trend was observed in viability. Although HL-60 cells incubated with either RA and ribose showed slight reductions in viability, the decline was more severe in the cells incubated with both RA and ribose. It can be noted that the control HL-60 cells averaged 92% viability, while cells treated with both RA and ribose averaged only 64% viability.

The reduced number of cells in the RA+D-Ribose cultures was due to reduced growth and not to an increase in the number of dead cells.

B. Cell Surface Markers of Maturity

Cell samples for the detection of cell surface molecules were prepared for flow cytometry in 12×17 mm capped conical tubes. To each tube, 30 $\mu$l of PBS containing 2% FBS was added. To each of triplicate tubes, a phycoerythrin (PE) labeled antibody (PharMingen, San Diego, Calif.) was added: 20 $\mu$l of CD1 1b, 20 $\mu$l of CD117, or 20 $\mu$l of isotype control (Mouse IgG1,κ). Fifty microliters of prepared cell suspension were added to each tube, followed by gentle mixing. Tubes were placed on ice for forty-five minutes after which 2 ml of cold PBS containing 2% FBS were added to each tube. Tubes were centrifuged (Jouann, at 300×g for 10 minutes) at approximately 5° C. and supernatant removed. One ml of cold 0.5% paraformaldehyde solution was added to the pellet and tubes were vortexed immediately. Prior to analysis, fixed cells were stored in the dark at approximately 4° C. for a period no longer than one week. Samples were analyzed on FACScan. Data were analyzed using WinMDI Software (Scripps Institute, build 1301-19-200, San Diego, Calif.).

Cells were labeled with propidium iodide and Annexin V-FITC for the detection of apoptosis as per the manufacturer's instructions (Kit 1, PharMingen). Briefly, cells were incubated with 0, 10 or 25 mmol/L ribose in the presence or absence of 1 mmol/L RA for 96 hours. They were harvested, washed and resuspended in binding buffer to which 5 $\mu$l of Annexin V-FITC and 2 $\mu$l of propidium iodide were added/ Cells were mixed gently, incubated for 15 minutes and analyzed by flow cytometry or fluorescent microscopy within one hour. Data were plotted and statistical analysis was performed using Cell Quest Version 3.3 software (BD Biosciences, San Jose, Calif.) running on a Macintosh G3 computer. Green vs. orange fluorescence data were displayed on a dot plot and quadrant markers were set on both axes at the upper limit of background based on the control, unstained sample. The percent of the cell population expressing Annexin V-FITC and negative for propidium iodide was quantitated. Positive controls used HL-60 cells incubated with 1 $\mu$mol/L camptothecin.

Figure 2:
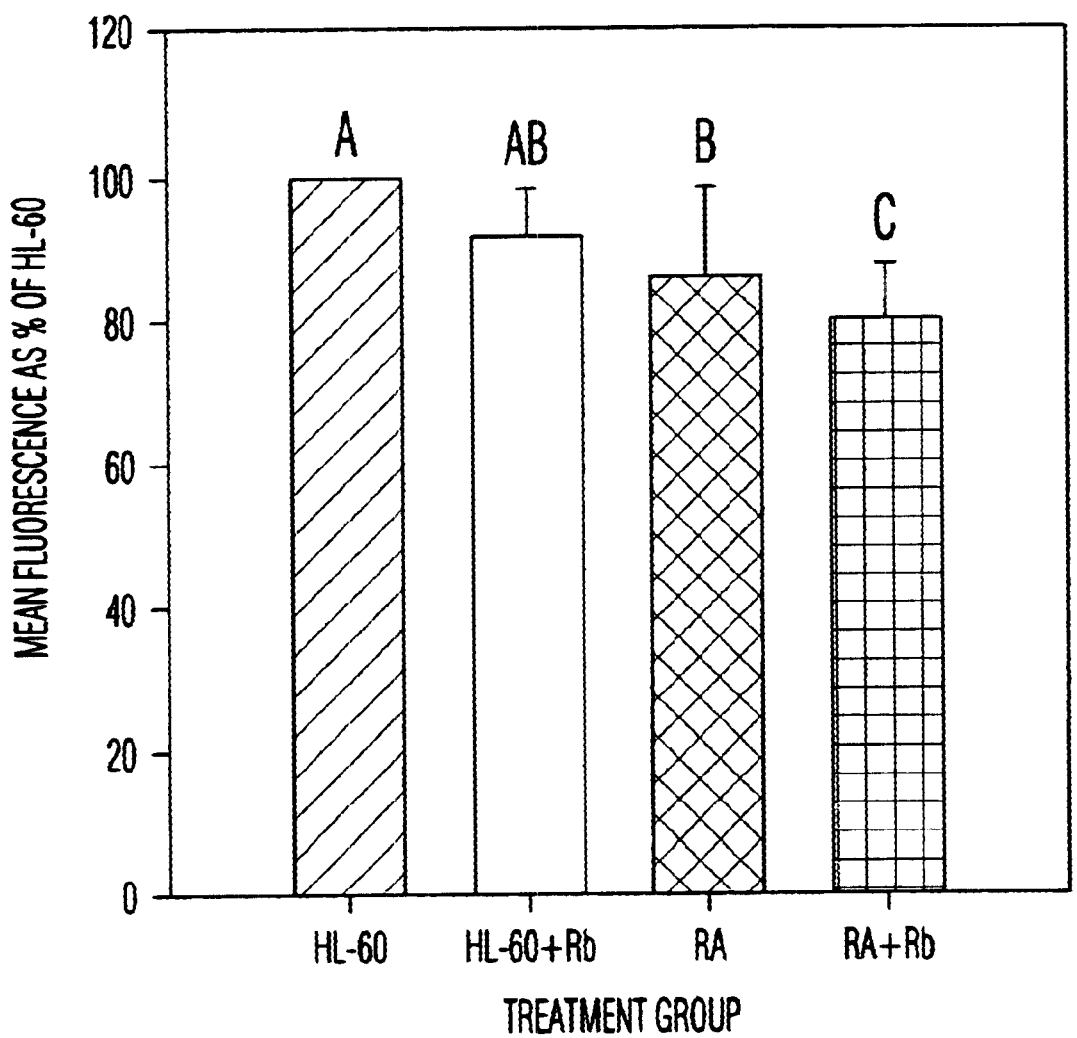
FIG. 2 shows the expression of immature cell markers on treated HL-60 cells.

Differentiation is accompanied by changes in the surface markers CD117 and CD11b. CD117 is a tyrosine kinase receptor that is expressed in high quantities on undifferentiated cells, while CD11b is a cell adhesion molecule expressed in high quantities on differentiated cells. After harvest, aliquots of the ribose and glucose control cells were allowed to differentiate with retinoic acid as above. An ELISA assay was set up with antibodies against CD117 or CD11b. At 10 mM ribose, there was a 30% reduction in CD117 and a threefold increase in CD11b. Expression of CD117 was linear with deceasing concentrations of ribose (1, 5 and 10 mM while CD11b appeared to have a threshold in which the highest expression of CD11b occurred at 10 mM ribose. FIG. 1 shows the characteristics of incubated cells. The expression of cell surface marker reactive with CD11b antibody is indicative of cell maturation. It can be seen that the cells treated with RA have a high level of expression of this cell surface marker, which is increased further by the addition of ribose. Conversely, the immature cell surface marker recognized by CD117 antibody is reduced (FIG. 2).

Table 2 summarizes the differentiated characteristics of HL-60 cells incubated with retinoic acid compared to those incubated with D-Ribose. Since D-Ribose is also known to be metabolized through glycolysis or gluconeogenesis, and because the addition to the culture medium raises the osmolarity, the characteristics of cells treated with D-Glucose in place of D-Ribose was investigated.

TABLE 2

Differentiated Characteristics of HL-60 Cells Incubated with Retinoic Acid or D-Ribose.

| | RA | RA + 10 mM Rb | RA + 10 mM glucose |
|---|---|---|---|
| Growth (cell/ml) | 7.27 ± 1.02$^A$ | 4.76 ± 1.06$^B$ | 7.23 ± 1.12$^A$ |
| Viability (%) | 82.6 ± 3.3$^B$ | 73.2 ± 7.7$^C$ | 86.6 ± 2.6$^A$ |
| CD11b (%) | 35.7 ± 7.5$^B$ | 41.1 ± 6.9$^A$ | 32.4 ± 6.8$^B$ |
| CD117 (%) | 33.4 ± 9.5$^A$ | 28.8 ± 6.7$^B$ | 31.2 ± 4.1$^A$ |

TABLE 2-continued

Differentiated Characteristics of HL-60 Cells Incubated with Retinoic Acid or D-Ribose.

| | RA | RA + 10 mM Rb | RA + 10 mM glucose |
|---|---|---|---|
| Respiratory Burst (% of RA control) | 100$^B$ | 147.4 ± 7.4$^A$ | 93.0 ± 7.9$^B$ |

Results are reported as mean ± SD for each group; n = 5. Values within a row having different superscript letters are significantly different, $p < 0.05$.

It is known that an inverse relationship exists between proliferation and maturation. Leukemic cell growth has been noted to diminish when cellular maturation is induced. The results shown here support that relationship. The normal course of leukocyte development is first, proliferation when the leukocytes are stimulated. Here, the leukocytes are immortal cells that do not require additional stimulation to proliferate. Non-immortal cells are generally stimulated to proliferate by mitogens. Leukocytes in vivo may be stimulated by exposure to bacteria or other antigens. Following proliferation, leukocytes divert their cellular resources to differentiation and maturation, as seen in these examples by treatment with RA. In vivo, normal leukocytes differentiate spontaneously. Finally, following maturation and having carried out their function, leukocytes in vivo undergo apoptosis, or programmed cell death.

C. ATP Determination

Determination of ATP was performed using a kit purchased from Sigma Diagnostics (St. Louis, Mo.) with slight modifications. 1.0 ml of 12% trichloroacetic acid (TCA) and 1.0 ml of prepared cell suspension ($1\times10^7$ cells/ml) were combined, vortexed and placed on ice for five minutes. Tubes were then centrifuged (Jouann, at 2000×g for 8 minutes) to obtain a clear supernatant. The following reagents were then added into vials containing 0.3 mg NADH: 1.0 ml phosphoglyceraldehyde buffered solution, 1.5 ml water, and 0.15 ml cell supernatant. Samples were distributed into two tubes. One tube was used to obtain an initial spectrophotometric absorbance at 340 nM. Fifteen $\mu$l of GAPD/PGK enzyme mixture were added to the second tube and read after ten minutes. Changes in absorbance were calculated and results were expressed as $\mu$mol of ATP per $1\times10^9$ cells.

HL-60 control cells had an ATP concentration of about five $\mu$moles per $10^9$ cells, which was slightly increased by the treatment with ribose. However, the addition of RA, with or without ribose, decreased the ATP concentration to below 4 $\mu$moles per $10^9$ cells.

D. Respiratory Burst

Specific cells undergo an increase in oxygen uptake when presented with appropriate stimuli, such as invading microorganisms or phorbol ester. The cells utilize this oxygen to produce a series of free radicals that kill the invading microorganism. Production of free radicals occurs via an enzyme called NADPH oxidase. Free radical production is measured spectrophotometrically by a change in color of ferricytochrome c.

The ability of cells to produce superoxide anion was measured by the reduction of ferricytochrome c via a microtiter plate (Levy et al (1990)). Fifty microliters of cells ($1\times10^7$ cells/ml) previously incubated with retinoic acid, ribose or glucose were plated in triplicate wells of a microtiter plate. Each well contained 10 $\mu$l of 1.5 mol/L ferricytochrome c substrate and 100 $\mu$l of DPBD containing 1 mmol/L glucose. Cells were stimulated to produce superoxide anion by addition of 10 μl of 1.6 μmol/L phorbol 12-myristate 13-acetate (PMA). A kinetic reading on dual wavelengths of 540–490 nM was taken using a Molecular Devices microtiter plate reader (UVMax, Menlo Park, Calif.). Change in absorbance was measured over ten minutes. In order to ensure that reduction of ferricytochrome was the result of superoxide anion, experimental samples were incubated with 10 μl of bovine erythrocyte superoxide dismutase (7500 units/ml). Addition of superoxide dismutase during assay resulted in the inhibition of color change; therefore, the change in optical density was due to the superoxide anion radical. Respiratory burst was expressed as the change in optical density/$10^6$ cells.

Figure 3:
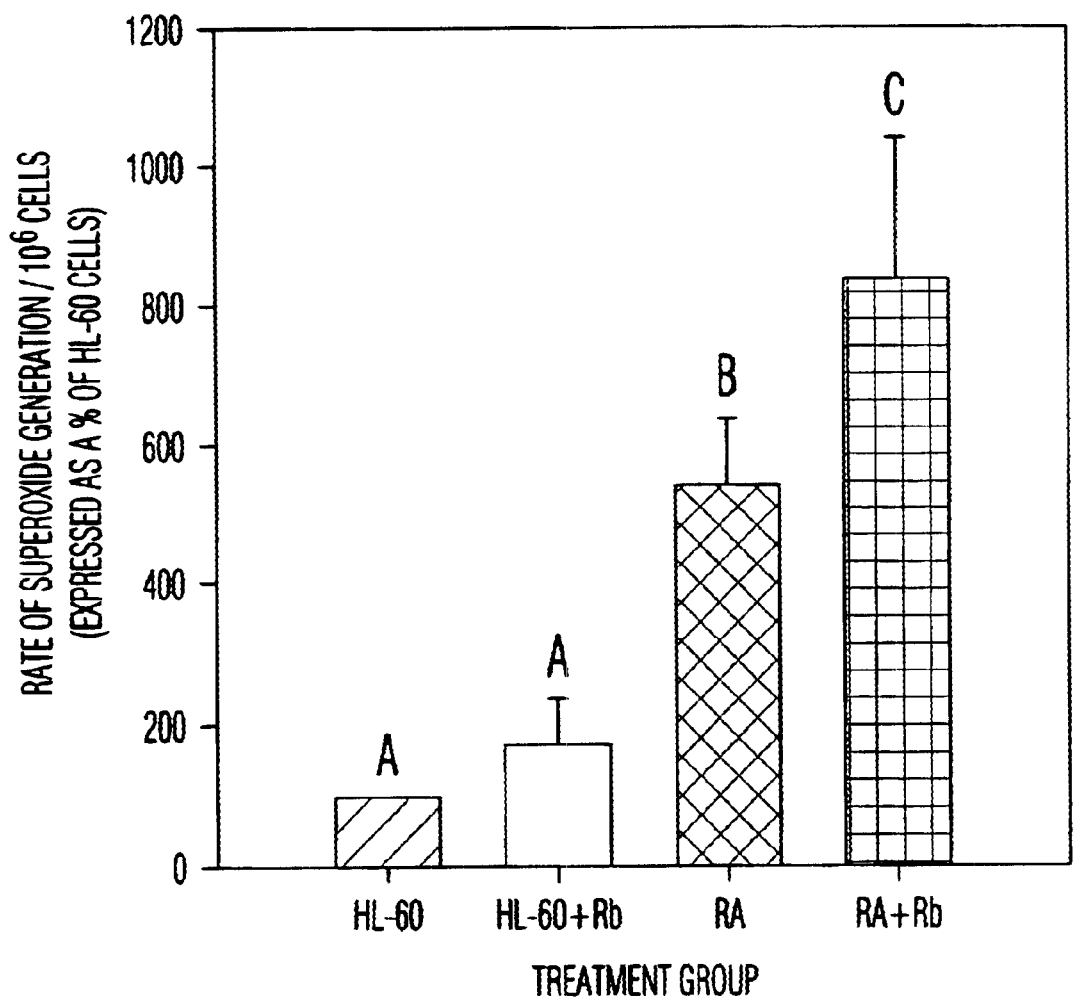
FIG. 3 shows the respiratory burst in treated cells.

Respiratory burst was significantly increased in cells treated with RA; however, the cells receiving ribose in addition to RA showed an even greater ability to carry out the oxidative burst (FIG. 3). When compared to the HL-60 control cells, there was a 5.5-fold increase in rate of superoxide generation within the RA treatment group versus an almost eight-fold increase in the RA plus ribose group. There was no significant increase in oxidative burst when HL-60 cells received ribose without being induced to differentiate via RA.

EXAMPLE 2

Normal Mouse Leukocytes

Mice are the species of choice for studies of the immune response because of the numerous nutritional and interventional studies that have been performed on mice. Details of its immune response are well studied and the inbred lines used eliminate any genetic differences. Spleens and thymus were removed from weanling Swiss ICR mice and cell suspensions prepared. The spleen and thymus cells were plated in a 96-well plate and various levels of ribose added to each well in triplicate. Phytohaemagglutinin (PHA), a T-cell stimulator, was added and the cells incubated for 48 hours. Tritiated Thymidine was then added, the cells harvested 24 hours later, and radioactivity incorporated was determined by liquid scintillation counting.

At low levels of ribose, there was a slight, but non-significant stimulation of spleen cell and thymus cell proliferation. The slight increase in proliferation found was consistent within the lowest concentrations tested, but was not dose responsive. Ribose above 5 mM tended to inhibit proliferation, which may have been due to a more pronounced switch from the proliferative mode tot he differentiation mode.

EXAMPLE 3

In Vivo Loading with Ribose

Figure 4:
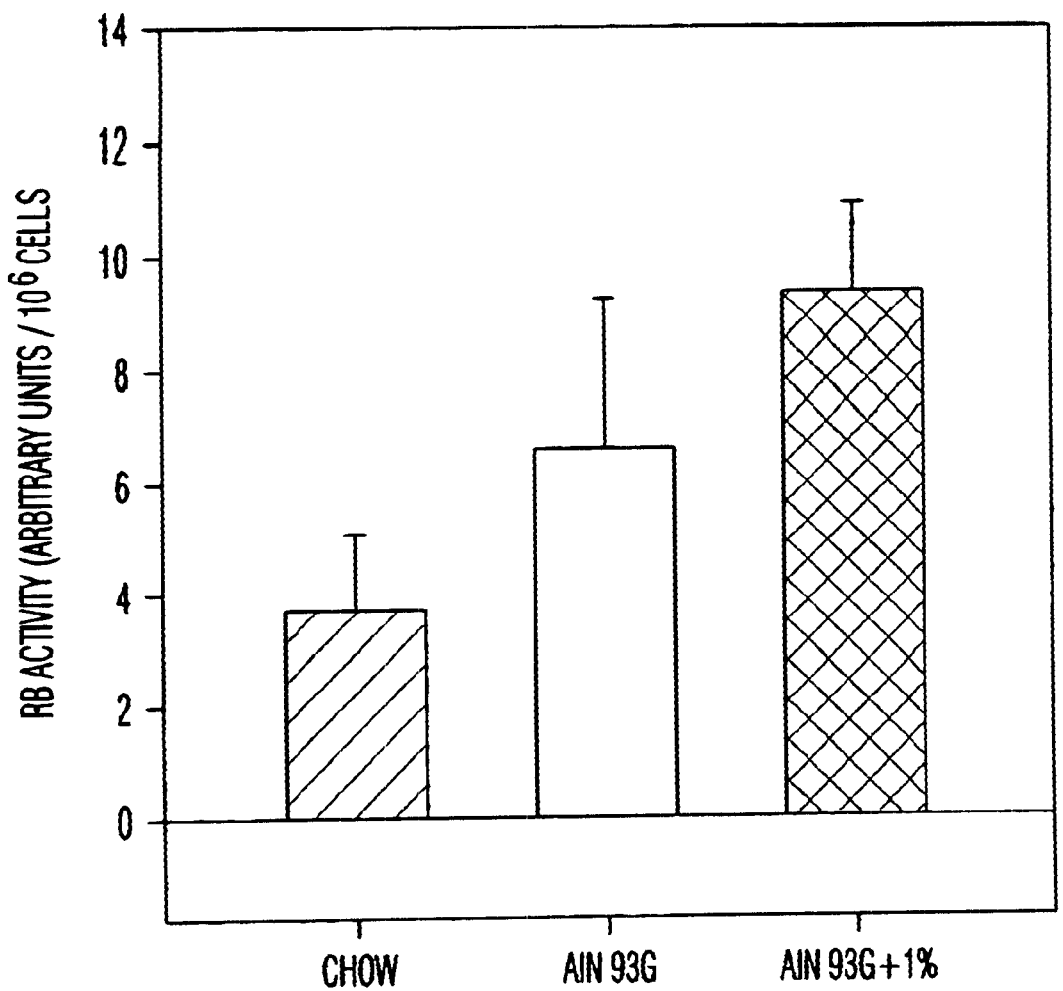
FIG. 4 shows the effect of D-Ribose in the diet on immune response.

For the in vivo studies, weanling Swiss ICR mice (three weeks old) were fed a fully nutritious, casein-based diet (AIN 93G). FIG. 4 shows the difference in immune response between animals fed the usual laboratory chow, those fed the AIN 93G diet and those fed the AIN 93G diet supplemented with 1% D-Ribose.

This pilate study will be followed by a broader study with ten animals per groups. Popliteal lymphoproliferation, delayed-type hypersensitivity (DTH) and thymic and splenic lymphocyte proliferation will be tested. To determine popliteal lymphoproliferation, the popliteal node will be excised and weighed after antigen injection into the hind-leg footpad. DTH can be assessed by measuring ear swelling after sensitization and stimulation with the prop antigen dinitrofluorobenzene. Thymic and splenic proliferation will be determined from cells isolated from the thymus and spleen and pulsed with tritiated thymidine. These four measures are all T-cell responses.

Another group of animals will be fed as above. Half of these animals will be used for baseline immune measures and half will be used after injection of lipopolysaccharide (LPS). T-cell numbers, proliferation and migration, B-cell numbers, NK cell numbers and migration, neutrophil numbers, migration and oxidative burst will be determined. Blood will be removed from the animals and fractionated on discontinuous gradients to collect lymphocytes and neutrophils. Cells will be quantitated by flow cytometry, oxidative burst will be determined spectrophotometrically and proliferation by incorporation of tritiated thymidine. Cell migration will be determined by flow cytometry as the percentage of cells. In addition, the activity of myeloperoxidase, a degradative enzyme specific to neutrophils, can be measured in lung tissue to determine this cell's migration.

In other studies, animals will be challenged with such bacterial pathogens as *Listeria monocytogenes, Staphylococcus aureus* and *Candida albicans*. Based on the in vitro studies of example 1 and 2, it is expected that D-Ribose will be shown to benefit the immune response as indicated by these parameters.

EXAMPLE 4

Ex Vivo Methods

Many patients with immune deficiencies will benefit from the enhancement of the immune response disclosed herein. If such patients have sufficient leukocytes, oral or parenteral administration with ribose can result in the proliferation, differentiation and maturation into fully functional immune cells, as seen in the cultured cells of Examples 1 and 2 and the in vivo stimulation seen in Example 3. It has been found with other uses of ribose that as little as 0.5 gm of D-Ribose may be sufficient to achieve a beneficial result, while as much as 20 gm is well tolerated. Preferably, D-Ribose is given more than once a day, preferably two or three times a day. Most adult patients are administered two to five gm of D-Ribose twice a day. Pediatric patients may be given a reduced dose, as indicated by body weight.

If the patient's condition allows, it is most beneficial to administer autogenous transfusions of the patient's own leukocytes which have been induced to proliferate and then differentiate in vitro, following the methods of Example 1. Still others may be so deficient in leukocytes that leukocyte transfusion from a donor or donors is necessary to provide them with adequate immune function. Such a transfusion will be more efficacious if the cells are cultured in the presence of ribose before transfusion as in the methods of Example 1.

It should be pointed out that in the in vitro methods of this invention, the cells must be artificially stimulated with retinoic acid, phytohemagglutinin or phorbol myristic acetate in order to show the effect of ribose. In vivo, many natural stimuli are present which fulfill the function of the added artificial stimulants.

All references cited within are incorporated by reference.

We claim:

1. A method for enhancing the immune response comprising:

(a) separating leukocytes from the blood of at least one donor mammal;

(b) culturing said leukocytes in a medium containing D-Ribose at a concentration of 2–20 millimoles per liter; and (c) introducing said cultured leukocytes transfused into a recipient mammal that would benefit from an enhanced immune response.

2. The method according to claim 1 wherein the leukocytes are separated from the blood of a donor mammal, cultured in the presence of D-Ribose and reintroduced into said donor mammal.

3. The method according to claim 1 wherein the D-Ribose concentration in said medium is from 5–15 millimoles per liter.

* * * * *